(12) United States Patent
Kobayashi (10) Patent No.: US 6,367,980 B1
(45) Date of Patent: Apr. 9, 2002

(54) ULTRA THIN TYPE ROLLING BEARING AND CAGE THEREFOR

(75) Inventor: Umemitsu Kobayashi, Kuwana (JP)

(73) Assignee: NTN Corporation, Osaka-fu (JP)

( * ) Notice: Subject to any disclaimer, the term of this patent is extended or adjusted under 35 U.S.C. 154(b) by 0 days.

(21) Appl. No.: 09/573,964

(22) Filed: May 19, 2000

(30) Foreign Application Priority Data

May 20, 1999 (JP) .......................................... 11-140267

(51) Int. Cl.⁷ .......................... F16C 23/00; F16C 33/60
(52) U.S. Cl. ........................ 384/517; 384/504; 384/506; 384/537
(58) Field of Search ................................ 384/490, 499, 384/500, 501, 502, 504, 505, 506, 512, 517, 518, 537, 540, 542, 543, 544, 563, 583, 584, 585, 589

(56) References Cited

U.S. PATENT DOCUMENTS

| | | | | |
|---|---|---|---|---|
| 4,784,438 A | * | 11/1988 | Fikse | 384/583 X |
| 4,990,000 A | * | 2/1991 | Harsdorff | 384/542 |
| 5,620,263 A | * | 4/1997 | Ohtsuki et al. | 384/517 |
| 6,099,167 A | * | 8/2000 | Goto et al. | 384/544 |

* cited by examiner

Primary Examiner—Thomas R. Hannon
(74) Attorney, Agent, or Firm—Arent Fox Kintner Plotkin and Kahn, PLLC (57) ABSTRACT

The bearing according to the invention is an ultra thin type rolling bearing in which the ratio of a ball diameter/a pitch circle diameter is 0.03 or less, and includes an outer member, an inner member, and balls inserted between these members. A double row raceway surface is provided at the inner circumferential surface of the outer member. The inner member includes an annular member and an engaging member engaged to the outer circumference of the annular member and having an axial clearance to the annular member, and raceway surfaces are provided at the outer circumferential surfaces of the annular member and engaging member. Preloading is performed by pressurizing the engaging member and reducing the axial clearance. Thus, the number of parts is reduced and the manufacturing cost is reduced accordingly.

3 Claims, 6 Drawing Sheets

ULTRA THIN TYPE ROLLING BEARING AND CAGE THEREFOR

BACKGROUND OF THE INVENTION

The present invention relates to an ultra thin type rolling bearing for use in an industrial robot, a machine tool, medical equipment or the like and a cage for such a rolling bearing.

Figure 8:
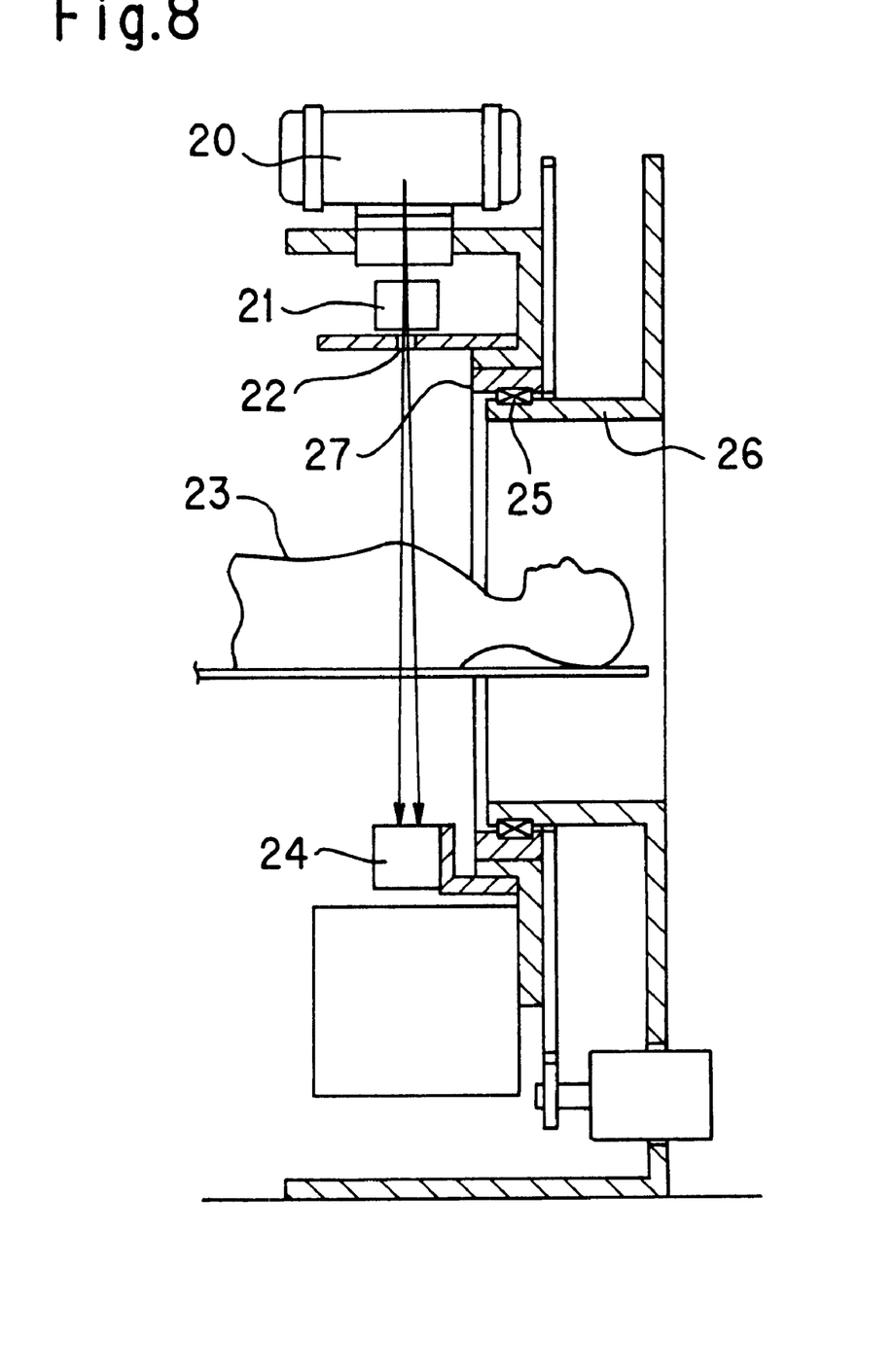
FIG. 8 is a cross sectional view of a CT scanner.

FIG. 8 shows a CT scanner, an example of one kind of medical equipment. As shown, in the CT scanner, an X ray generated by an X ray tube assembly 20 is directed upon an object 23 through a wedge filter 21 to equalize the intensity distribution and a slit 22 to restrict the intensity distribution. The X ray passed through the object 23 is received by a detector 24, converted into an electrical signal and transferred to a computer which is not shown. Elements such as the X ray tube assembly 20, wedge filter 21, slit 22 and detector 24 are mounted on an approximately cylindrical, rotary pedestal 27 supported rotatably around a stationary pedestal 26 through a bearing 25, and driven to rotate by the rotary pedestal 27 around the object 23. In the CT scanner, the rotating movement around the object 23 of the X ray tube assembly 20 and the detector 24 opposing to each other results in projection data covering all the angles at every point within a cross section of the object 23 to be examined, and a cross sectional image is obtained based on these pieces of data using a pre-programmed reconstruction program.

Figure 9:
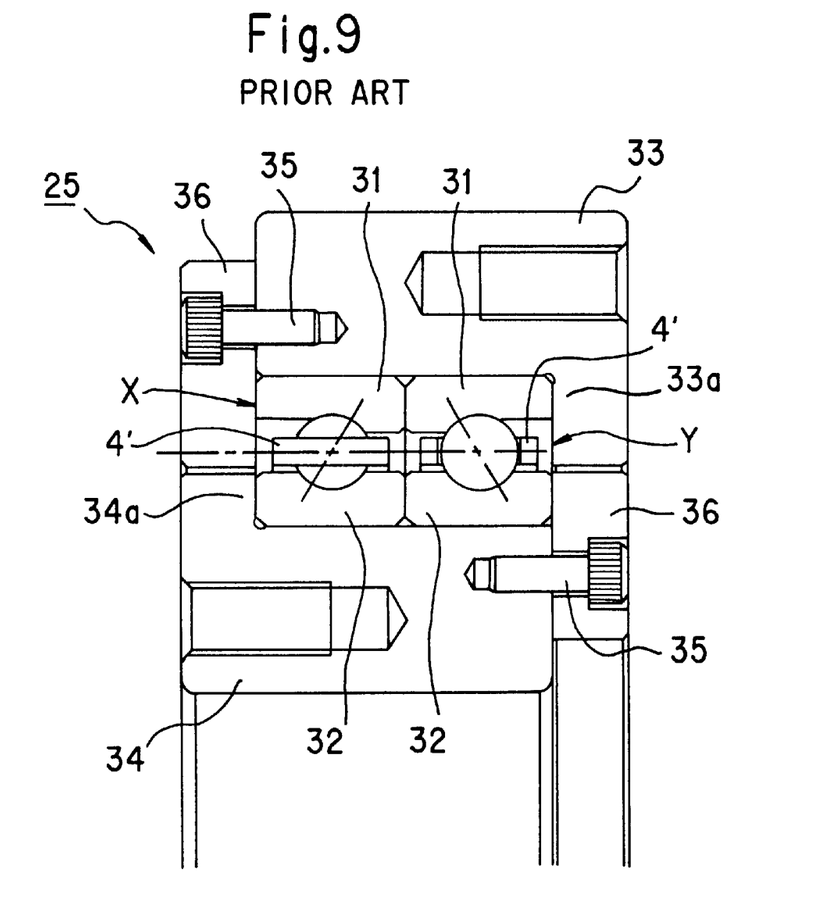
FIG. 9 is a cross sectional view of a conventional ultra thin type rolling bearing.

In the CT scanner, the inner circumferential surface of the stationary pedestal 26 has a large opening to let the object 23 therein (approximately 1 m in diameter), and therefore a so-called ultra thin type rolling bearing having a cross section significantly small relative to the diameter is used for the bearing portion 25 between stationary pedestal 26 and rotary pedestal 27. Among such ultra thin type rolling bearings, a so-called combination angular contact ball bearing formed by combining two angular contact ball bearings X and Y as shown in FIG. 9 is used, particularly when such a bearing is used at a high rotating speed of about 120 rpm or higher. The combination angular contact ball bearing as shown is a so-called back-to-back arrangement having the two angular contact ball bearings X and Y with their back faces (faces which can receive the thrust load) in contact with each other, and pressurizing force is allowed to act upon in the direction in which the outer ring 31 (outer member) of one bearing X and the inner ring 32 (inner member) of the other bearing Y face each other, so that appropriate preload is applied to the inside of the bearings for use.

According to the conventional device, the outer annular body 33 is threadedly secured to one pedestal (the rotary pedestal 27, for example), and inner annular body 34 is threadedly secured to the other pedestal (the stationary pedestal 26, for example). Each outer rings 31 of the two bearings X and Y is engaged to the inner circumferential surface of the outer annular body 33, while each inner ring 32 of the two bearings X and Y is engaged to the outer circumferential surface of the inner annular body 34, so that the rotary pedestal 27 is rotatably supported. A presser member 36 is secured to each of one end side of inner annular body 34 and the other side of outer annular body 33, using a fastening screw 35, and the presser members 36 press the end surfaces of the outer ring 31 and inner ring 32, and the end surfaces on the opposite side are received by shoulder portions 33a and 34a provided at the outer annular body 33 and inner annular body 34, respectively, so that preload is applied to the inside of the bearings.

Figure 10A:
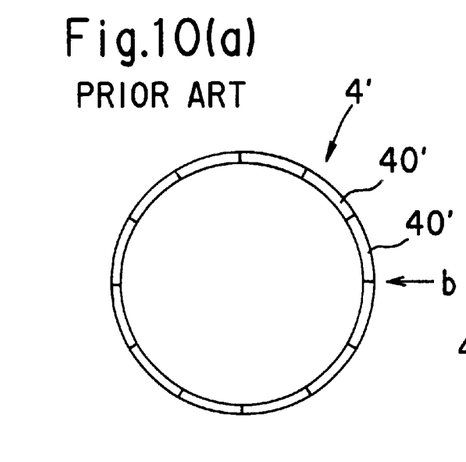
Figure 10B:
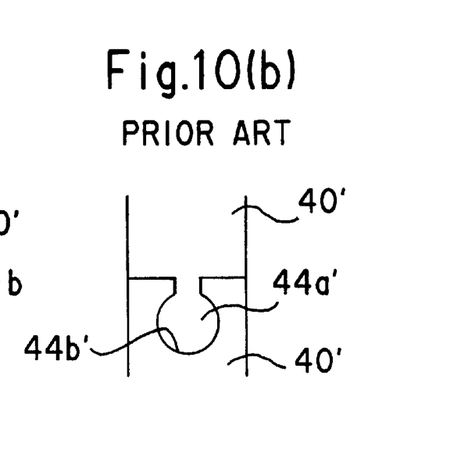

In the conventional ultra thin type rolling bearing for the CT scanner as described above, a cage 4' of resin is used. The resin cage 4' is of a separate type cage formed into an annular shape by connecting a plurality of segments 40' having a circular cross section as shown in FIG. 10(a), and in the conventional device, recessed or raised engaging portion 44a', 44b' are formed at the ends of each segment 40' as described in FIG. 10(b), and the recessed or raised engaging portion 44a', 44b' is engaged to raised or recessed engaging portion 44b', 44a' at the segment end to be coupled therewith, so that they are engaged with each other in the circumferential direction to couple each segment 40'.

The conventional ultra thin type rolling bearing for the CT scanner is assembled with a large number of parts including the outer and inner annular bodies 33 and 34, presser members 36, in addition to the bearing parts such as the outer rings 31 and inner rings 32 as described above. Since such a large number of parts are necessary, the precision of each part would be added up to lower the entire precision, and therefore, strict precision control is demanded for each part. Furthermore, since the bearing portion is extremely thin, if the deviation from circular is even slightly deviated than allowed for the inner and outer annular bodies, the bearing ring bends along the shape, which adversely affects the performance of the bearing, and therefore the outer and inner rings should also be finished with high precision. As a result, the part and assembly cost for the conventional bearings has been increased and there is a strong demand for cost reduction.

Also in the conventional resin cage, segments are coupled with their recessed and raised engaging portions as described above, but the engagement between the recessed and raised engaging portions can be loose depending upon the formation error at the time of forming the resin. In this case, individual segments tend to shift toward the inner and outer diameter sides, which may cause oscillation when the rotating speed is increased. In order to solve this problem, the recessed and raised engaging portions should be formed with high precision but realizing this requires much work including correction of forming molds, which pushes up the cost.

SUMMARY OF THE INVENTION

It is therefore an object of the present invention to reduce the number of parts and reduce the manufacturing cost as a result. Another object of the present invention is to securely and less costly prevent the coupling portions of a separate type cage from being shifted in the circumferential and radial directions.

In order to achieve the above-described objects, an ultra thin type rolling bearing according to the present invention includes an outer member having a double row raceway surface in which a rolling element rotates at its inner circumferential surface, an inner member provided on the inner circumferential side of the outer member, formed of an annular member and an engaging member engaged at the outer circumference of the annular member with an axial clearance with respect to the annular member, and provided with raceway surfaces in which rolling elements rotate at respective outer circumferential surfaces of the annular member and the engaging member, rolling elements inserted in two rows between the outer and inner members and having a diameter whose ratio relative to a pitch circle diameter is 0.03 or less, and a preloading means for pressurizing the engaging member to reduce the axial clearance for preloading.

Alternatively, the ultra thin type rolling bearing may include an outer member having a double row raceway surface in which a rolling element rotates at its inner circumferential surface, an inner member provided on the inner circumferential side of the outer member, formed of an annular member and a pair of engaging members engaged at the outer circumference of the annular member with an axial clearance therebetween, and provided with raceway surfaces in which rolling elements rotate at respective outer circumferential surfaces of both engaging members, rolling elements inserted in two rows between the outer and inner members and having a diameter whose ratio relative to a pitch circle diameter is 0.03 or less, and a preloading means for pressurizing one engaging member to reduce the axial clearance for preloading.

An ultra thin type rolling bearing according to the present invention may include an outer member, an inner member provided on the inner circumferential side of the outer member, a plurality of rolling elements inserted between the inner member and the outer member and having a diameter whose ratio relative to a pitch circle diameter is 0.03 or less, and a cage having a plurality of pockets each retaining a rolling element, formed into an annular shape by coupling a plurality of resin segments, and provided with engaging portions at coupling portions with adjacent segments to matingly engage the coupling portions of the corresponding side segments in the circumferential and radial directions.

In the case, the circumferential engaging portions to matingly engage the coupling portions of the corresponding side segments in the circumferential direction and radial engaging portions to matingly engage said coupling portions in the radial direction may be discretely or integrally provided.

One of the above described outer and inner members may be secured at the rotary pedestal of a CT scanner rotating around an object, and the other may be secured at the stationary pedestal of the device.

A cage for an ultra thin type rolling bearing according to the present invention is used in an ultra thin type rolling bearing in which the ratio of a rolling element diameter and a pitch circle diameter is 0.03 or less. The cage has a plurality of pockets to retain rolling elements. The cage is formed into an annular shape by coupling a plurality of resin segments and is provided with engaging portions at coupling portions with adjacent segments to matingly engage the coupling portions of the corresponding side segments in the circumferential and axial directions.

Also in this case, the circumferential engaging portions to matingly engage the coupling portions of the corresponding side segments in the circumferential direction and the radial engaging portions to matingly engage said coupling portions in the radial direction may be discretely or integrally provided.

The nature, principle, and utility of the invention will become more apparent from the following detailed description when read in conjunction with the accompanying drawings in which like parts are designated by like reference numerals or characters.

BRIEF DESCRIPTION OF THE DRAWINGS

FIGS. 4($a$) ($b$) is an enlarged view of one coupling portion of a segment, where ($a$) is a plan view and ($b$) is a view seen from the direction of arrow b in ($a$);

FIGS. 5($a$) ($b$) is an enlarged view of the other coupling portion of the segment, where ($b$) is a plan view and ($a$) is a view seen from the direction of arrow a in ($b$);

FIGS. 6($a$) ($b$) is an enlarged view of one coupling portion of a segment, where ($a$) is a plan view, and ($b$) is a view seen from the direction of arrow b in ($a$);

FIGS. 7($a$) ($b$) is an enlarged view of the other coupling portion of the segment, where ($b$) is a plan view and ($a$) is a front view seen from the direction of arrow a in ($b$);

FIGS. 10($a$)($b$) is a view of a cage, where ($a$) is a side view thereof and ($b$) is a plan view seen from the direction of arrow b in ($a$).

DESCRIPTION OF THE PREFERRED EMBODIMENTS

Embodiments of the present invention will be now described in conjunction with FIGS. 1 to 9.

Figure 1:
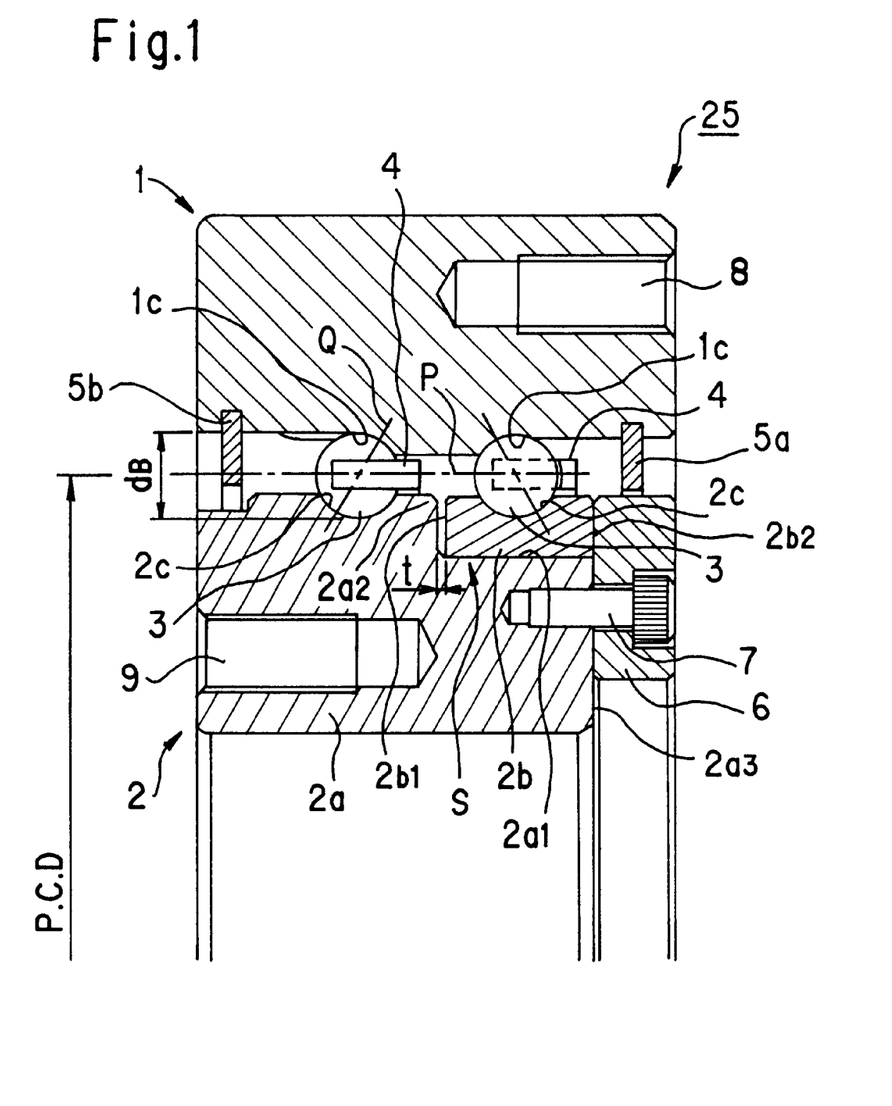
FIG. 1 is a cross sectional view of an ultra thin type rolling bearing according to the present invention.

FIG. 1 shows the structure of the bearing 25 in the CT scanner shown in FIG. 8. The bearing 25 includes, as main elements, a ring-shaped outer member 1, a similar, ring-shaped inner member 2 concentrically disposed on the inner circumferential side of the outer member 1, rolling elements 3 inserted between the inner member 2 and the outer member 1, a cage 4 to retain the rolling elements 3 at equal intervals in the circumferential direction, seals 5$a$, 5$b$ to seal the openings at both ends of the bearing, and a preloading means S to preload the inside of the bearing.

The bearing 25 is a double row bearing having two rows of the rolling elements 3, and in this embodiment, a double row angular contact ball bearing having balls 3 as the rolling elements arranged in two rows is disclosed by way of illustration. The combination of both bearing portions are the same as the case of the back-to-back arrangement as shown in FIG. 9, the intersection of lines of action Q of the rolling element load is outside the pitch circle P. The contact angle of both bearing portions (the angle formed by the direction of the rolling element load and a plane perpendicular to the central line of the bearing) is set for example to 30°.

This double row angular contact ball bearing is an ultra thin type rolling bearing where the ratio φ of the diameter dB of the ball 3 and the pitch circle diameter PCD is 0.03 or less (φ=dB/PCD≦0.03). The diameter of the ball is set for example to ½ inch (12.7 mm), PCD is set to 1041.4 mm, and their ratio φ is set to 0.012.

The outer member 1 includes the conventional outer ring 31 and outer annular body 33 as shown in FIG. 9 integrally formed with each other, and raceway surfaces 1$c$ on which the balls 3 rotate are formed in two rows corresponding to the numbers of rows of the balls 3 at its inner circumferential surface.

The inner member 2 includes an annular member 2$a$ including conventional, one inner ring 32 and inner annular body 34 which are integrally formed, and a ring shaped engaging member 2$b$ engaged to the outer circumference of the annular member 2$a$. There is a stage portion 2$a$1 having a diameter smaller than the other part at the outer circumferential surface at one end portion of the annular member 2$a$, and the engaging member 2$b$ is securely engaged to the stage portion 2a1. There are raceway surfaces 2c at the outer circumferential surfaces of the annular member 2a and engaging member 2b, and the balls 3 are inserted between these two raceway surfaces 2c and the two raceway surfaces 1c of the outer member 1.

The preloading means S used to appropriately preload inside of the bearing by pressurizing the engaging member 2b toward the inside of the bearing for example has the following construction.

The engaging member 2b is securely engaged to the annular member 2a in such a loose fit degree that it can be moved by tightening by the presser member 6 as will be described. Before the presser member 6 is tightened, there is an axial clearance t between the shoulder portion 2a2 of the annular member 2a and the end surface 2b1 on the other end side (the left in the figure) of the engaging member 2b, and an end surface 2b2 on one end side (the right in the figure) of the engaging member 2b slightly axially projects from the end surface 2a3 on the one end side of the annular member 2a. The projection amount at this time is equal to or slightly larger than the width of the axial clearance t.

At the end surface on one end side of the outer member 1, there is formed an attachment hole 8, into which a bolt is tightened, so that the outer member 1 is secured to the rotary pedestal 27 of the CT scanner shown in FIG. 8. At an end surface on the other end side of the inner member 2 (the end surface on the other end side of the annular member 2a in this embodiment), there is also provided an attachment hole 9, into which a bolt (not shown) is tightened, so that the inner member 2 is secured to the stationary pedestal 26. Thus, the outer member 1 serves as a rotating member to rotate together with the rotary pedestal 27, and the annular member 2a and engaging member 2b forming the inner member 2 serve as a non-rotating, stationary member. Depending upon the structure of the CT scanner, the outer member 1 may be on the non-rotating, stationary side while the inner member 2 may be rotated together with the rotary pedestal 27, contrary to the above.

At an end surface on one end side of the annular member 2a, the ring-shaped, presser member 6 is secured with a fastening means 7 such as a bolt. The outer radial end of the presser member 6 is substantially in the same level as the outer circumferential surface of the engaging member 2b. Among the pair of seals described above, the seal 5a on one end side is located at a position opposing the outer radial end of the presser member 6.

In the above described construction, when the fastening means 7 is fastened, the presser member 6 pressurizes and forces the engaging member 2b into the inside of the bearing. This allows the above described preloading means S to function and cause the axial clearance t to be reduced, and the pressurizing force is transmitted to the outer member 1 through the balls 3, so that the outer member 1 is pressed into the other end side in the axial direction. As a result, a bearing clearance of both bearing portions is filled and the appropriate preload is applied. The width of the initial axial clearance t is predetermined so that a prescribed amount of preload is obtained at the point when engaging member 2b is pressed into and the axial clearance t is 0, and thus the preload can be adjusted at a high precision and by a simple operation. Alternatively, a method of controlling the tightening torque of the fastening means 7 for example may be employed to apply a prescribed amount of preload upon the bearing portion (in which case, the axial clearance t is not necessarily 0 after the pressurization).

In the above construction, the number of parts can be reduced for the outer ring 31 and one presser member 36 as compared to the conventional product as shown in FIG. 9, and therefore the part cost or assembly cost can be reduced. In addition, higher precision is allowed for the reduced number of parts, and finishing processing to achieve corresponding precision can be simplified to further reduce the cost.

Figure 2:
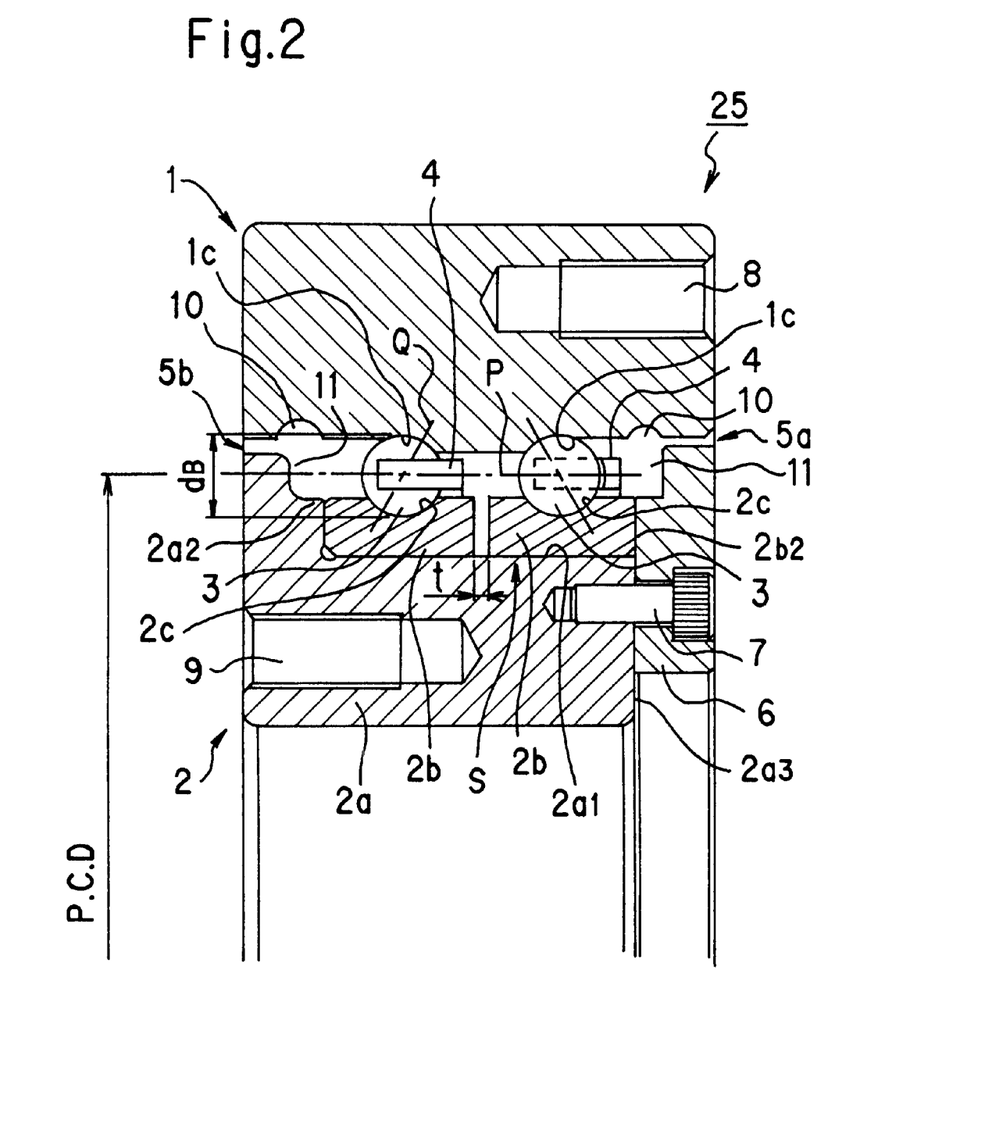
FIG. 2 is a cross sectional view of another embodiment of the invention.

FIG. 2 shows another embodiment of the present invention. This bearing is also a double row, ultra thin type angular contact ball bearing where the ratio $\phi$ of the ball diameter dB/the pitch circle diameter PCD is set to 0.03 or less similarly to the case shown in FIG. 1. The bearing is formed by engaging a pair of engaging members 2b to a stage portion 2a1 provided at the outer circumferential surface of the annular member 2a, and raceway surfaces 2c are provided at respective outer circumferential surfaces of the engaging members 2b. The engaging member 2b on the other end side is engaged by a shoulder portion 2a2 provided at the outer circumferential portion at the other end of the annular member 2a. There is an axial clearance t between both engaging members 2b, and the presser member 6 is tightened so that the clearance t is reduced. This allows the preloading means S to function, and a prescribed amount of preload is applied to the inside of the bearing.

In FIG. 2, seals 5a, 5b to enclose both opening portions of the bearing are shown as being formed as non-contacting type seals by extending the outer radial ends of the annular portion 2a and presser member 6 to the outer radial side into close proximity to the inner circumferential surface of the outer member 1, but non-contacting type seal members such as seal washers 5a, 5b may be attached to the outer member 1 similarly to FIG. 1. It is understood that contacting type seals may also be employed. There is an annular lubrication groove 10 at the inner circumferential surface of the outer member 1 and between seals 5a, 5b and both raceway surfaces 1c, and an oil trap 11 is formed by trimming at the outer circumferential surfaces of the annular member 2a and presser member 6 opposing this lubricant groove 10. The differences from FIG. 1 are mainly described above, while the other features, functions and effects, modifications are substantially identical to those of the embodiment shown in FIG. 1. Therefore, common portions are denoted with the same reference characters and the same description is not provided.

The cage 4 of the above double row, angular contact ball bearing is a separate type resin cage similarly to the conventional product as shown in FIG. 10(a), and is formed into an annular shape by connecting a plurality of segments 40' having a circular cross section.

Figure 3:
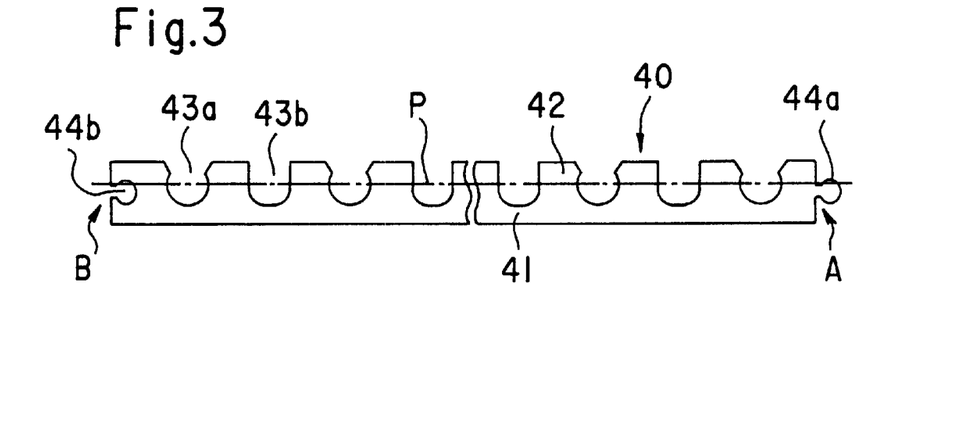
FIG. 3 is a developed, plan view of a segment forming a cage.

FIG. 3 is a developed plan view of the segment 40. Segment 40 as shown includes bases 41 formed by dividing an annular body at a plurality of positions in the circumferential direction and having a circular shape, a columnar portion 42 extending in one axial direction from the base 41, and a plurality of pockets 43a, 43b provided between adjacent columnar portions 42. The columnar portion 42 extends in one axial direction beyond the pitch circle P of the ball 3. The pockets 43a and 43b as shown have two kinds of shapes, one of which is the shape of a first pocket 43a having its wall surface near the opening side of the pocket rather than the center shaped as a recessed circular surface when two-dimensionally viewed, and the other is the shape of a second pocket 43b having an axially straight wall surface. The first and second pockets 43a and 43b are provided alternately in the circumferential direction. Any of the wall surfaces of the pockets 43a and 43b is a concave surface whose center of curvature is at the center of the pocket in a radial cross section. The balls 3 are stored into the pockets 43a and 43b by pressing the balls 3 into the backside of pockets from the axial openings of pockets 43a and 43b. At this time, the balls 3 must be pressed in while forcing columnar portions 42 open on the inlet side, while no such operation is necessary for the second pocket 43b, so that the process of incorporating the balls 3 into the cage 4 can be simplified. Note that the shapes and structures of the above-described pockets 43a and 43b are only by way of illustration, and the pockets may be of the same shape, for example, in other words, pockets of various shapes and structures may be used depending upon the conditions for using the bearing.

On both ends of each segment 40, coupling portions A and B to couple adjacent segments are provided. The coupling portions A and B have two shapes, a coupling portion of one of the shapes is provided on both ends of each segment 40. At both coupling portions A and B, there are provided two kinds of engaging portions to matingly engage with the corresponding coupling portions of the segments in the circumferential and radial directions, in other words, circumferential engaging portions 44a and 44b to matingly engage with the corresponding coupling portions in the circumferential direction, and radial engaging portions 45a and 45b to matingly engage with the corresponding coupling portions in the radial direction are provided (see FIGS. 4 and 5).

Figures 4A, 4B:
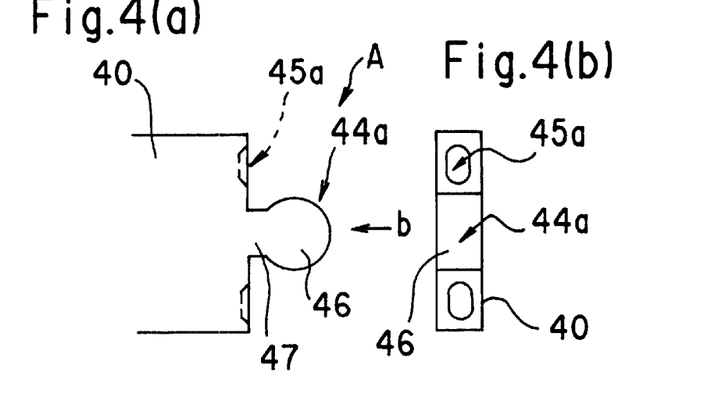

The circumferential engaging portion 44a at one coupling portion (A in FIG. 3) has a raised shape broader on its tip side, and includes for example a substantially cylindrical, engaging portion 46 which extends in the radial direction, and a narrow portion 47 having a narrower width than engaging portion 46 in the axial direction as shown in FIG. 4. The radial engaging portion 45a at the coupling portion A has a recessed shape, and formed on both sides of the axial direction of the raised circumferential engaging portion 44a and in a part of the radial region (for example in the central part in the radial direction) of the cage 4. The raised circumferential engaging portion 44a may have another shape as long as it is wider at its tip (such as a trapezoid), and the recessed radial engaging portion 45a may have any shape as long as a part of the radial region of the cage 4 is recessed.

Figures 5A, 5B:
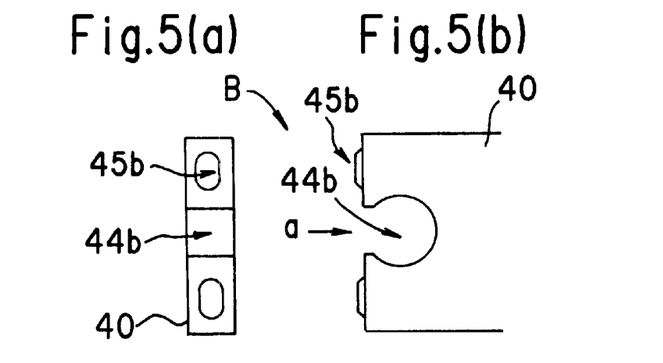

As shown in FIG. 5, the circumferential engaging portion 44b at the other coupling portion B is formed to have a recessed shape to conform to the raised circumferential engaging portion 44a as described above. The radial engaging portion 45a at the coupling portion B has a raised shape to conform to the recessed radial engaging portion 44a as described above.

Adjacent segments in the above described structure are coupled by pressing one coupling portion (for example A) into the other coupling portion (for example B) in the radial direction. After the coupling, the circumferential engaging portions 44a and 44b are matingly engaged to prevent the segments from being separated from one another in the circumferential direction, while the radial engaging portions 45a and 45b are matingly engaged to prevent the segments from being separated from one another in the radial direction. At this time, if the circumferential engaging portions 44a and 44b are loosely engaged with each other, a fastening margin is provided to the coupling portions A and B as the radial engaging portions 45a and 45b are engaged with each other, so that the segments 40 will not wobble with each other and can be securely coupled.

In FIGS. 4 and 5, at one coupling portion (for example A), the circumferential engaging portion 44a and the radial engaging portion 45a are shown as a combination of recessed and raised portions, respectively, but the engaging portions 44a and 45b may be both formed into a recessed or raised shape.

Figures 6A, 6B:
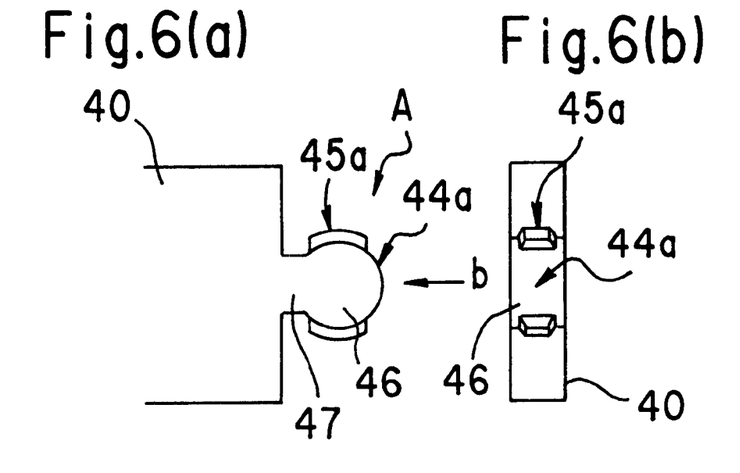
Figures 7A, 7B:
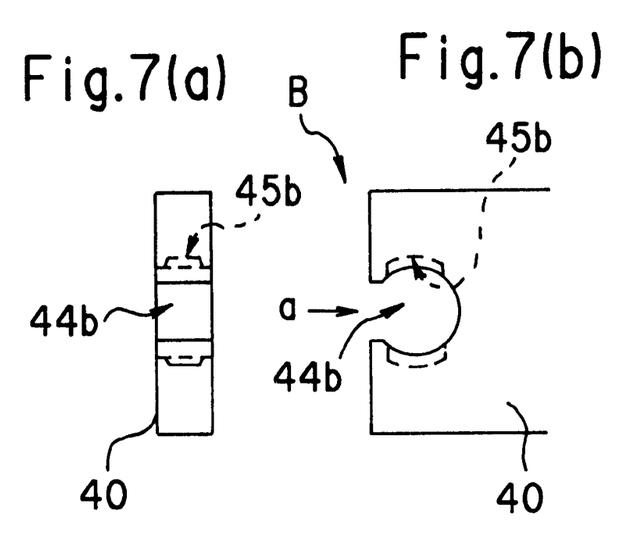

Another embodiment of the coupling portions A and B is shown in FIGS. 6 and 7. In FIGS. 4 and 5, at both coupling portions A and B, the circumferential engaging portions and radial engaging portions (44a, 45a) (44b, 45b) are provided as discrete bodies, while in FIGS. 6 and 7, at both coupling portions A and B, the circumferential and radial engaging portions (44a, 45a) (44b, 45b) are integrally provided and the same effects as the construction in FIGS. 4 and 5 are brought about. In the figures, both engaging portions 44a and 45a have a raised shape at one coupling portion (for example A), but one of the engaging portions may have a recessed shape.

As described above, according to the present invention, the number of parts can be reduced as compared to the conventional structure, which reduces the cost of parts and the cost of assembly. In addition, higher precision is more readily allowed for the reduced number of parts, and finishing processing to achieve corresponding precision can be simplified. Accordingly, the cost can be further reduced and higher precision can be achieved.

At the coupling portions of adjacent segments, there are provided engaging portions which matingly engage with the coupling portions of the corresponding segments in the circumferential and radial directions, and therefore a fastening margin is provided between the coupling portions between the segments, so that the coupling portions of the segments are engaged in two directions, i.e., in the circumferential and radial directions. As a result, the segments may be surely coupled and the cage will not cause noise at increased speeds.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An ultra thin type rolling bearing, comprising:
   an outer member having a double row raceway surface in which a rolling element rotates at its inner circumferential surface;
   an inner member provided on the inner circumferential side of the outer member, formed of an annular member and an engaging member engaged at the outer circumference of the annular member with an axial clearance with respect to the annular member, said inner member being provided with raceway surfaces in which rolling elements rotate at respective outer circumferential surfaces of the annular member and the engaging member;
   rolling elements inserted in two rows between the outer and inner members and having a diameter whose ratio relative to a pitch circle diameter is 0.03 or less; and
   a preloading means for pressurizing the engaging member to reduce said axial clearance for preloading.

2. An ultra thin type rolling bearing, comprising:

an outer member having a double row raceway surface in which a rolling element rotates at its inner circumferential surface;

an inner member provided on the inner circumferential side of the outer member, formed of an annular member and a pair of engaging members engaged at the outer circumference of the annular member with an axial clearance therebetween, said inner member being provided with raceway surfaces in which rolling elements rotate at respective outer circumferential surfaces of both engaging members;

rolling elements inserted in two rows between the outer and inner members and having a diameter whose ratio relative to a pitch circle diameter is 0.03 or less; and a preloading means for pressurizing one engaging member to reduce said axial clearance for preloading.

3. The ultra thin type rolling bearing according to claims 1 or 2, wherein one of the outer member and inner member is secured at the rotary pedestal of a CT scanner rotating around an object, and the other is secured at the stationary pedestal of the device.

* * * * *